United States Patent [19]

Smit

[11] 4,315,509
[45] * Feb. 16, 1982

[54] INSERTION AND REMOVAL CATHETERS AND INTESTINAL TUBES FOR RESTRICTING ABSORPTION

[76] Inventor: Julie A. Smit, 1045 Hinman Ave., Evanston, Ill. 60602

[*] Notice: The portion of the term of this patent subsequent to Jan. 16, 1996, has been disclaimed.

[21] Appl. No.: 951,864

[22] Filed: Oct. 16, 1978

Related U.S. Application Data

[63] Continuation-in-part of Ser. No. 757,929, Jan. 10, 1977, Pat. No. 4,134,405.

[51] Int. Cl.³ .............................................. A61B 17/00
[52] U.S. Cl. .................................. 128/303 R; 128/1.4; 128/6; 128/348; 128/356; 417/474; 3/1
[58] Field of Search .................. 128/1 R, 1.3, 1.4, 6, 128/8, 303 R, 132 R, 348, 349 R, 349 B, 349 BV, 350 R, 350 V, 356, DIG. 9; 3/1; 417/474

[56] References Cited

U.S. PATENT DOCUMENTS

| | | | |
|---|---|---|---|
| 750,735 | 1/1904 | Turck | 128/24 R |
| 2,268,321 | 12/1941 | Flynn | 128/349 R |
| 2,508,690 | 5/1950 | Schmerl | 128/276 |
| 2,706,979 | 4/1955 | Wallace | 128/1.4 |
| 2,799,274 | 7/1957 | Eisenhut | 128/356 |
| 2,971,471 | 2/1961 | Huebschman | 417/474 |
| 3,395,710 | 8/1968 | Stratton | 128/350 R |
| 3,511,583 | 5/1970 | Brown | 417/474 |
| 3,610,231 | 10/1971 | Takahashi | 128/6 |
| 3,736,939 | 6/1973 | Taylor | 128/239 |
| 3,811,423 | 5/1974 | Dickinson et al. | 128/1 R |
| 3,834,394 | 9/1974 | Hunter et al. | 128/348 |
| 3,913,565 | 10/1975 | Kawahara | 128/8 |
| 3,960,143 | 6/1976 | Terada | 128/4 |
| 4,057,065 | 11/1977 | Thow | 128/348 |
| 4,134,405 | 1/1979 | Smit | 128/303 R |
| 4,140,126 | 2/1979 | Chouphury | 128/325 |
| 4,148,319 | 4/1979 | Kasper et al. | 128/349 B |

FOREIGN PATENT DOCUMENTS

| | | | |
|---|---|---|---|
| 1945805 | 3/1971 | Fed. Rep. of Germany | 417/474 |
| 885054 | 12/1961 | United Kingdom | 128/348 |
| 279885 | 3/1971 | U.S.S.R. | 128/356 |

OTHER PUBLICATIONS

Carlson, Anton J. et al.; *The Machinery of the Body*; 5th Ed. ©1961, p. 330.
Wallechinsky, David et al.; *The People's Almanac*; p. 1058.

*Primary Examiner*—Robert W. Michell
*Assistant Examiner*—Arthur S. Rose
*Attorney, Agent, or Firm*—J. Warren Whitesel; Charles Laff; Larry Saret

[57] ABSTRACT

A first part of the inventive instrument comprises an insertion and removal device in the form of a maneuverable catheter which may be inserted through the mouth or nostril, pharynx, and esophagus into the stomach. In one form, the catheter includes an outer sheath which protects the human body while a tool extending coaxially through an inner sheath is being manipulated. The tool includes a remotely operated pair of tweezers for holding or releasing a loop on insertion or seizing and holding the loop on removal of the second part of the inventive instrument. An alternate device for capturing and holding the second part of the inventive instrument uses an electromagnet. The second part of the inventive instrument comprises a self-compressing, open-ended, balloon-like tube for implantation in and lining of the digestive tract, especially in the intestine, to prevent food from being absorbed into the villi. The balloon-like tube expands outwardly when filled with food chemicals, enabling peristalsis to squeeze the food chyme through the tube. An alternate embodiment intermittently lines only desired areas of the alimentary canal. The tube may also be used to treat obesity or alcoholism, or to cover an ulcer and give it an opportunity to heal with minimum exposure to digesting food and gastric juices.

41 Claims, 22 Drawing Figures

INSERTION AND REMOVAL CATHETERS AND INTESTINAL TUBES FOR RESTRICTING ABSORPTION

This is a continuation-in-part of my co-pending patent application Ser. No. 757,929 filed Jan. 10, 1977 and entitled "Catheter and Intestine Tube and Method of Using the Same," now U.S. Pat. No. 4,134,405.

This invention relates to medical appliances and more particularly to devices for lining body passages, especially—although not exclusively—to devices for lining portions of the human alimentary canal.

The instrument for implantation in the alimentary canal comprises a self-compressing, open-ended tubular device for transporting untreated food which has been consumed in a normal manner through the mouth of the person having the implanted device. In the normal digestive process, the food becomes partially digested and liquefied before coming into contact with the implanted instrument which can be anchored in the pyloric part of the stomach. When the partially digested food chemicals enter the implant, they are squeezed through the tube by the normal peristaltic movements and contractions, in the patient's body. The tubular implant retains a very narrow or collapsed diameter when empty of food chemicals and expands outwardly as food chemicals enter. Thus, when the intestinal walls feel a change in diameter, they commence peristaltic movements and contractions which squeeze the liquefied chyme through the tubular implant and then out its open end.

There are many times when it may be desirable to provide such a tube for lining a passage in a human or animal body in order to control, prevent or restrict a transfer of chemicals through the walls of the passage. Exemplary of such a lining is a tube extending through portions of the small intestine in order to prevent or restrain digesting food from there being absorbed by the body. This lining may be used to restrict absorption and thereby serve as a treatment for obesity, alcoholism, ulcers, or the like.

Consider the particular problems of obesity by way of example. Some people are unable to lose weight under any normal procedures. Therefore, in the past, they have submitted to surgical treatment wherein portions of the intestine have been bypassed to reduce the absorption area of the intestine. However, there have been undesirable side effects when such surgical treatment is used. For example, these side effects have included uncontrollable diarrhea, electrolytic imbalance, unpredictable weight loss, reflex of nutritious chyme proximal to the site of anastomsis, failure in the anticipated degree of bypass, and even death. Thus, there is a need for a less drastic method for reducing the absorption area of the intestine, without resorting to surgery.

Accordingly, an object of the invention is to control the effective absorption area of a passageway in an animal body. Here, an object is to control the absorption surface area of the human alimentary canal, without having to resort to irreversible procedures, such as surgery or dangerous drugs such as amphetamines. In particular, an object is to line or cover a large portion of the absorption area of the intestines in order to reduce or prevent absorption by means of a reversible procedure which may be undone if unwanted side effects persist.

Another object of the invention is to line or cover a larger portion of the intestinal villi, causing them to reduce in size owing to their reduced use.

Another object of the invention is to cover an ulcerated portion of the intestine so that it may have time to heal without being exposed to the digestive process, especially the stomach's hydrochloric acid.

Still another object of the invention is to cover a portion of the intestinal absorption area for treatment of obesity.

Yet another object of the invention is to accomplish these and other objects without affecting normal body processes (such as gastro-intestinal reflexes, glandular secretions) or causing excessive, unwanted peristalsis, and the like. Here, an object is to accomplish these objects in a manner which may be reversed if unwanted side effects should occur.

In keeping with an aspect of the invention, these and other objects are accomplished by use of a two-part instrument. The first part of the instrument is an insertion and removal device in the form of a catheter for lining the throat which may be used to protect it from mechanical damage during insertion and removal of the second part of the instrument, without requiring an operation. An inner sheath contains a tool for holding or releasing a loop or tab on insertion or seizing and holding a loop or tab on removal of the second part of the instrument. The tool within the inner sheath of the catheter may have either of two different embodiments. A first embodiment of the tool comprises a remotely operated pair of tweezers for grasping and holding a loop on the implant. An alternative embodiment of the tool means comprises an electromagnet for attracting a metallic tab on the second part of the inventive instrument.

The second part of the instrument is an extremely thin-walled tube containing a lengthwise, semi-flexible support which prevents the tube from twisting and bunching up, especially while being implanted in the gastrointestinal tract. The semi-flexible support means may be either of two alternative structures. One support means is an interrupted chain which is semi-rigid in one direction to prevent twisting and is flexible in another direction to adapt it to the contours of the intestinal tract. The other support means is a flat spring which is flexible in all dimensions. The spring stabilizes the thin-walled tube while reducing the possible erosion to the pyloric part of the stomach, which may be used to anchor the implant in place.

The implant for restricting absorption has two alternative embodiments. One lines a portion of the gastrointestinal tract with a continuous, collapsible tube and the other is interrupted to line only desired portions of the tract while bypassing other areas.

An added advantage of the implant is that it may be designed to have an effect upon villi size. The villi of overweight people are larger than the villi of thin people. Larger villi absorb more food chemicals than small villi absorb, during the digestive process. Therefore, if an overweight person and a thin person eat the same meal, the overweight person's body absorbs more of the food chemicals than the thin person's body absorbs. The size of a person's villi is determined, to a large extent, by the frequency of their use. When the implant which covers the villi is removed, after a period of continuous usage, the villi will have shrunk in size owing to their reduced usage. The shrunken and smaller villi do not absorb as much food chemicals as they absorbed when they were larger and, therefore, the person is less prone to regain the weight which has been lost.

The nature of preferred embodiments of the invention may be understood best from a study of the attached drawings, wherein:

FIG. 1 is a schematic diagram showing the inventive tube implanted in the small intestine, and the catheter in a position where it is about to be used to remove the implant;

FIG. 2 schematically shows, somewhat in perspective, a long thin-walled, balloon-like tube which may be implanted in a small intestine;

FIG. 3 shows in two views (in two perpendicular planes), a flat, semi-flexible chain having two flexure modes encased in a support tube, FIG. 3A being taken along line 3A—3A of FIG. 3B and FIG. 3B is taken along line 3B—3B of FIG. 3A;

In the description which follows, any suitable medical grade of plastic, or other material may be used. At present, it is thought that a silicone material should be used, such as "Silastic," for example, for the implanted tubes. "Silastic" is a registered trademark for Dow Corning's silicone elastomer materials, and related products. Information on this material is contained in Bulletin: 51-247; date: Sept. 1975, which is available from the Medical Products Business Division of Dow Corning Corporation, Midland, Mich., 48640.

According to this bulletin, "Silastic" is a clear, seamless material designed for use in a variety of clinical and laboratory applications. The material is easy to clean and is specifically suited for surgical drains, suction equipment and catheter applications, and for general hospital applications which demand inertness, non-reactivity, stability to heat and aging, and non-reaction to body tissue and fluid. It contains no plasticizers or additives to leech out, and it will not support bacterial growth. It has a soft pliability which contributes to a significant reduction in tissue irritation normally associated with long-term catheterization. It resists fatigue with repeated flexing or stretching. It is a non-wetting silicone elastomer with a surface that minimizes blood platelet destruction and contact hemolysis resists clotting, sticking, or incrustation, and assuring an excellent flow characteristic. Regardless of whether "Silastic" material is or is not used, the material should have these characteristics.

This or other suitable material is used to make the inventive two-part instrument. The first part of the instrument is a catheter 20 (FIG. 1) which is used as an insertion or removal device or tool which may be inserted through the mouth or nostril, pharynx, and esophagus into the stomach. The catheter 20 includes an outer sheath 22 which protects the esophagus and other body parts from abrasion or irritation while the tool 24 is being manipulated inside the inner sheath 60. The tool includes a remotely operated pair of tweezers 26 for holding or releasing a loop 28 on insertion or removal of the second part of the instrument, which is a tubular implant 30.

Tubular implant 30 (FIG. 2) includes a long and extremely thin-walled, balloon-like tube 32 which contains a semi-flexible, flat chain 34. Tubular implant 30 is designed to be implanted in the pyloric part of the stomach and extend into the intestine in order to cover the villi and limit or prevent the absorption of food, calories, alcohol, or the like.

The combination of the catheter and tubular implant 30 with a slow-dissolve gelatin capsule 100a (FIG. 2) on end 40 is pushed down the throat and into the stomach of the patient. Current medical treatment includes an employment of catheters which are so forced into the gastrointestinal tract in this manner. Therefore, the tubular implant 30 may be worked into the stomach and intestine in a known manner.

Figures 1, 2, 3A, 3B:
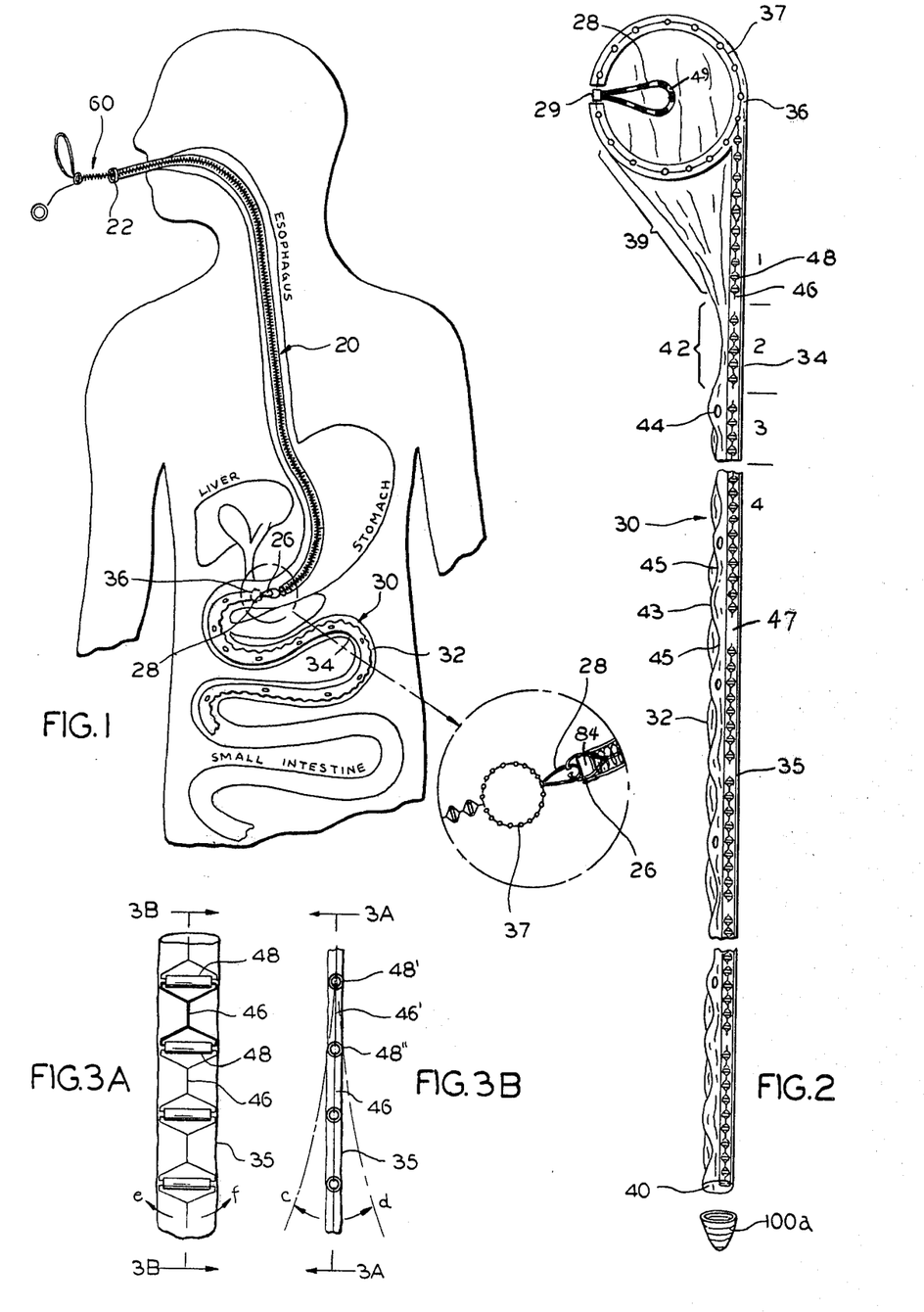

Tubular implant 30 includes a very thin-walled tube 32, which compresses into a very narrow diameter when empty of food chemicals, so that it does not induce excessive peristalsis or excessive glandular secretions while it is implanted in the intestine. Furthermore, because the walls of the tube are very similar in thickness to a balloon and because the walls of the tube lack rigid support, the small intestine does not tend to gather itself and bunch up along the tube, as often happens on catheters with thicker and more rigid tubes. For example, it is not uncommon for the entire small intestine to gather itself along perhaps a three-foot section of fairly stiff tubing and then to pass any remaining tubing out the anus. Since tube 32 is balloon-thin and very supple, it does not support the small intestine and, therefore, prevents gathering of the intestine. The small intestine adapts itself to the tube in the same manner that it adapts to food solids. Yet, the thin walls of tube 32 are strong enough not to rupture and are impervious to the passage of food chemicals which, therefore, are not absorbed through the adjacent portion of the intestine wall that is lined by the tube.

Both tube 32 and chain 34 terminate at one end in a retaining ring with a loop 28 attached to ring 36 by means of a tiny turnable tube 29 (i.e., tube 29 rotates about the axis of the ring 36 circumference). When more permanent implants are required, the ring 36 may be stitched or surgically stapled in position to anchor tube 32.

The chain 34 within tube 32 is interrupted periodically (as at 47) to enable an approximately normal intestinal movement. The interrupted chain 34 has two modes of flexure in its non-flexible mode, the chain supports the thin walls of tube 32 and prevents it from twisting and shutting off the transport of food solids responsive to the peristaltic movements in the intestine. The chain 34 also has a flexible mode so that it may curl and follow the natural intestinal path. The periodic interruptions in chain 34 enable some degree of flexible intestinal movement, in the non-flexible mode of the chain, without enabling tube twisting.

In greater detail, the duodenum or first nine to ten inches of the small intestine is the only portion of the small intestine which is attached to the body. The remainder of the small intestine is not attached to the body, but merely folds freely in a sack called the mesentery, which is contained within the peritoneum. This free-folding allows random intestinal motion, so that each intestinal section can accommodate itself to changes in form and position. Therefore, the small intestine more or less accommodates itself to the dimensional movements of the semi-flexible support chain 34. The flexible mode of the chain and the interruptions within the rigid mode of the chain tend to accommodate and enable full vertical and horizontal intestinal movement while the chain in the areas of its rigid mode tends to prevent the thin walls of tube 32 from twisting shut relative to the peristaltic movements in the intestine.

The stomach ring 36 expands under the resilience of the silicone encasing a section 37 of the semi-flexible chain. The chain section 37 within ring 36 is not interrupted and is rigid in the direction in which it would have to collapse, in order to pass through the pylorus and out the stomach. Therefore, the rigid mode of ring 36 implants itself against the stomach walls to anchor the end position of the tube 32. Yet, ring 36 is sufficiently flexible in the up and down dimensions in order to adjust with and conform to the contours of the pyloric stomach and its up and down peristaltic squeezing contractions. The stomach's squeezing contractions act upon the flexible mode of ring 36 to propel the food chemicals into ring 36 and tube 32.

Ring 36 fits snugly in the pyloric portion of the stomach to anchor and hold the tube 32 in place while it is in the intestine. Preferably, this anchoring occurs because the ring 36 is too large to pass through the sphincter muscle which opens wide enough to pass about an object which is approximately one cubic centimeter or less.

Ring 36 is of a size which needs to be compressed prior to insertion into and removal from the body. One method for compressing the ring is by grasping loop 28 with tweezers 26 and pulling ring 36 in the flexible mode and into the end of the catheter. Tube 32 is compressed when empty of food chemicals.

The walls of the ring 36 are contours to enable an easy entrance of food into the intestine. Attached to the back of the ring 36 is the balloon-like, thin-walled tube 32, which begins with a funnel-shaped section 39. Then, there is a portion 42 having a reduced diameter, which goes through the pylorus and, thereafter, the tube opens to approximately the inside diameter of the small intestine. The tube curves through the small intestine, following the normal intestine path. This embodiment of the implant does not bypass the common bile and pancreatic ducts which empty into the small intestine at points near the pylorus. The reason why tube 32 may rest over the ducts without obstructing them is because this portion of the duodenum has permanent folds called valvulae conniventes. These permanent folds are approximately $\frac{1}{4}$–$\frac{1}{3}$ inch in depth and are very large and numerous in the area of the ducts. Therefore, tube 32 rests upon the crests of the permanent folds and does not come into direct contact with the ducts. Other embodiments of the implant bypass different areas by interrupting the tubing.

The walls of the tube are periodically pierced by oval holes, one of which is seen at 44. These oval holes 44 are preferably about $\frac{1}{4}''$ long $\times$ $\frac{1}{8}''$ wide. They are punched through the tube walls so that the patient receives a controlled amount of nutrition in the area of the holes and so that the food inside the tube receives intestinal digestive juices. This way, the food leaving the tube will be in approximately the normal state of digestion, for that part of the intestine—only the amount of absorption into the villi is changed. If very few, widely spaced holes are provided in tube 32, only small amounts of food chemicals will escape for absorption into the villi. If a greater number of closely spaced holes are provided in tube 32, a greater amount of food chemicals will escape for absorption into the villi.

Tube 32 may be manufactured without any holes and in a few standard lengths. The doctor prescribing the implant determines the needs of the patient and then cuts the tube to the desired length and uses the oval hole punch of FIG. 9 to punch the holes, where desired, along tube 32 in order to fit each patient's individual needs.

Figures 9, 10, 10A, 10B, 11, 11A:
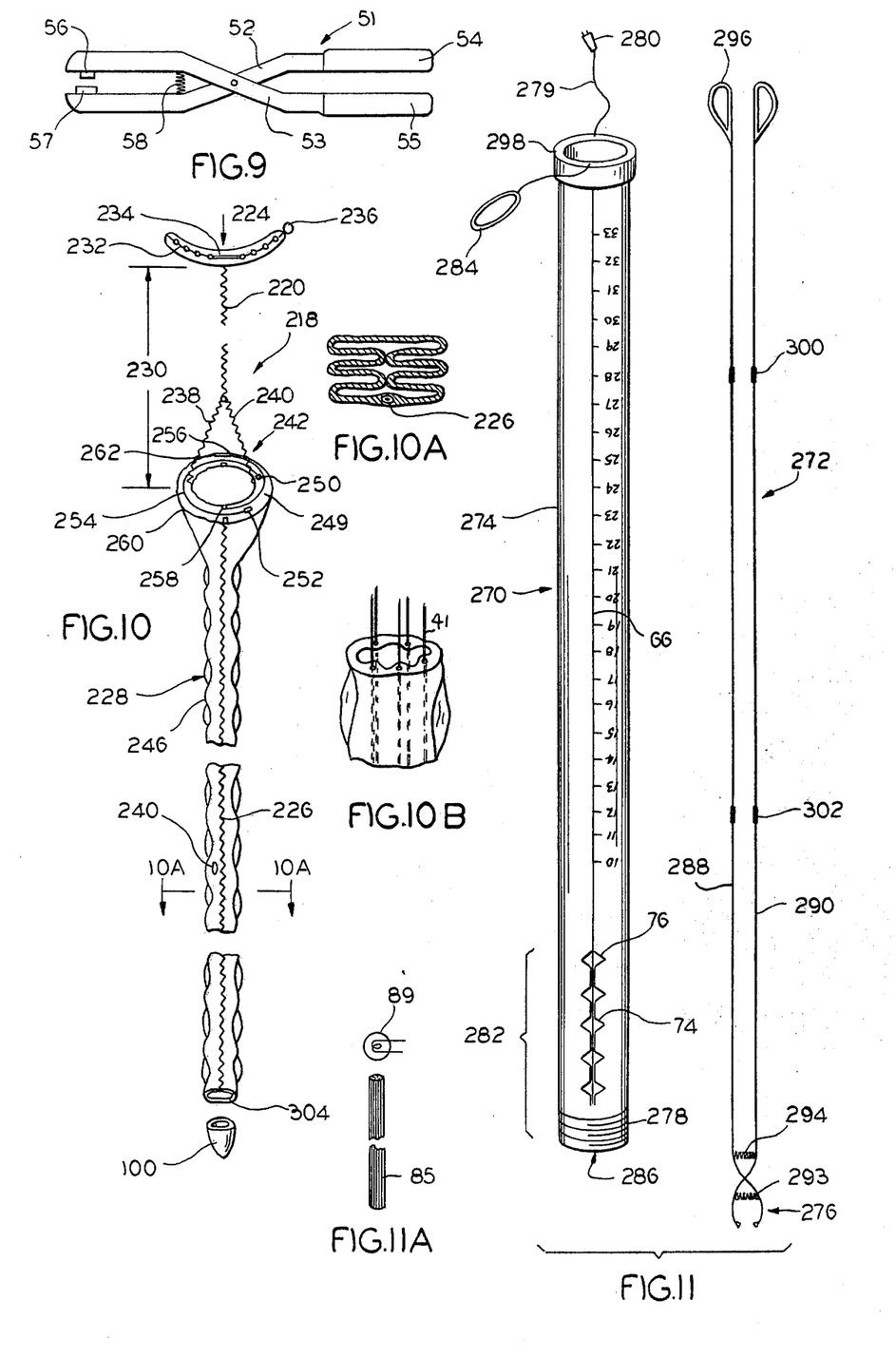
FIG. 9 shows a device used by a doctor for punching oval holes in desired areas of the inventive tube, in order to best fit the implant to each patient's individual needs.
FIG. 10 schematically shows, somewhat in perspective, a long balloon-like tube which is held a predetermined, desired distance away from its anchoring means by an elongated spring section which bypasses the tubular lining around areas of the gastrointestinal tract.
FIG. 10A shows the empty tube of FIG. 10 in a folded condition for insertion.
FIG. 10B shows the tube of FIG. 10 with reinforced walls.
FIG. 11 is a perspective view of the main parts of an electromagnetic catheter which combines features of the catheter of FIG. 4 with the electromagnet of FIG. 6B.
FIG. 11A shows the catheter of FIG. 11 with fiber optical strands for lighting the lower end of the catheter.

In greater detail, the oval hole punch 51 has two pivotally interconnected scissor-like lever members 52,53, each having a handle portion 54,55 on one end. Member 53 has a protruding oval punch 56 and member 52 has a mating die 57. The two scissor-like lever members 52,53 are held together by a tensioned spring 58. In operation, when handles 54 and 55 are drawn together, the protruding oval punch 56 cuts tube 32 as it moves into the die 57, thereby punching a hole 44 through tube 32. Preferably, the oval hole punch would cut holes approximately ¼"×⅛" into tube 32.

The number of holes and the length of the tube may vary widely, depending upon the desired medical effects. Preferably, the tube length is in the range of ½ foot to 7½ feet. For example, a tube 4-6 inches in length could be used to cover and treat ulcers of the duodenum, which are the most common. Duodenal ulcers are aggravated and prevented from healing because the stomach's hydrochloric acid is constantly emptying onto the ulcer, thereby eroding it further. If a short version of the implant lines the ulcerated portion of the duodenum, the food chemicals and gastric juices bypass the ulcerated portion and, upon leaving the tube, are neutralized by pancreatic secretion.

The stomach ring 36 and funnel-shaped tube section 39 begin about 1⅓" in diameter and narrow into about ⅝". The tube diameter remains at approximately ⅝" for about 1½"-2" in region 42, which is a length that is sufficient to fully pass through the pylorus and to accommodate any shifting or pulling which may occur responsive to the peristaltic waves of the stomach and intestine.

After section 42, and continuing throughout the remaining length of the tube 32, its walls are molded to gradually billow and constrict as seen at 43,45, respectively, to follow and conform to the interior of the intestine. The gradually billowed and constricted tube may be more maneuverable around the intestinal curves than a tube of one uniform diameter. Most important, the gently billowed and constricted walls prevent the tube's walls from becoming too taut as they follow around an intestinal coil, which would greatly narrow the food passageway within the tube.

The billowing (as at 43) begins about 3¾" from the stomach ring 36 (well beyond the pylorus) and continues for the length of the tube. Preferably, any suitable number, such as approximately four to eight lengthwise accordion folds (FIG. 10A) are molded along the entire length of the tube 32 with the number of folds depending upon the total reduction which is desired for tube implantation. These folds reduce the apparent outside diameter of the tube to approximately ¼" or less, until the tube fills with food. Food is squeezed into and through the tube 32 by the normal peristaltic wave motion in the stomach and intestine. As a result, the food causes the longitudinal folds in the tube 32 to open, and the walls of the tube to bulge outwardly. The intestine feels this bulge and the normal peristaltic wave motion results. Thus, until tube 32 is distended by food, it is and remains in a compressed form.

The balloon-thin walls of tube 32 may be reinforced as seen in FIG. 10B with reinforcing strands 41 (such as catgut or other material) which run longitudinally within the lengthwise accordion folds. These strands are used when the thin walls of tube 32 need additional strength to counteract the peristaltic pull on the tube.

The balloon-thin walls of tube 32 are kept stable and prevented from twisting by means of the semi-flexible, flat chain 34 which is enclosed and secured inside of both tube 32 and ring 36. Preferably, the flat chain 34 is slightly wider than the inside diameter of its encasement, tube 35, when in its originally manufactured condition. The encasement, tube 35, keeps the chain 34 from bunching and tends to hold it in a somewhat straight path. When the tube 32 curves around the intestine bends, chain 34 bends within its encasement tube 35, to correspond with the curve. The chain 34, its encasement tube 35 and tube 32 are the same length. Preferably, the encasement tube 35 runs along one side of and is integral with the tube wall.

The term "semi-flexible" is used herein to mean a device such as the chain section shown in FIG. 3, for example. More particularly, FIG. 3 shows a section of chain 34 within its encasement tube 35. Chain 34 is one exemplary means for stabilizing the thin walls of tube 32 in order to prevent it from twisting responsive to the peristaltic movements within the gastrointestinal tract. Chain 34 is interrupted periodically, as 47, and each section of chain 34 has two modes of flexure. The interrupted areas 47 between the chain sections are flexible in the entire 360° surrounding the longitudinal axis of the chain, to the extent that its encasement tube 35 is flexible. The rigid mode of chain 34 supports the balloon-thin walls of tube 32 while the periodical interruptions, within this rigid mode, enable tube 32 to adjust to the horizontal or sideways movement of the intestine. The vertical or up and down dimension of chain 34 is flexible.

In greater detail, FIG. 3 shows one exemplary chain section which is made from a plurality of links fashioned from rigid rods, wires, or plastic sections 46. Each link may be thought of as two "Y" members with their stems integrally attached together (for ease of identification, one of the sections is outlined in heavily inked lines in FIG. 3A). The arms on each end of each "Y" embrace and somewhat loosely fit into a tubular member, as at 48. Thus, for example, each of the links 46 may swing freely within its associated tubes 48 with motion in directions c,d (FIG. 3B). This means that the chain is almost completely flexible in directions c,d. On the other hand, there is very little give in a plane (FIG. 3A) which are taken at right angles to the flexible plane. The arms of the "Y" prevent movement in directions e,f. In its insertion condition, the tube 35 is transversely stretched slightly by the chain 34, thereby giving a greater stability in the flexible directions c,d. Encasement tube 35 helps to straighten the path of chain 34 in its flexible dimensions c,d in order to prevent the chain 34 from bunching. Encasement tube 35 also supports and prevents tube 32 from twisting in the interrupted areas 47 of chain 34.

The chain 34 and its encasement 35 give tube 32 enough support to prevent its thin walls from twisting and bunching during insertion into the body and enough support to later stabilize the tube against twisting responsive to the peristaltic movements and contractions, while the instrument is implanted within the alimentary canal. Furthermore, tube 32 is flexible enough to accommodate itself to the intestinal coils and for the intestine to accommodate itself to the tube. Most importantly, since tube 32 is flexible, the small intestine does not bunch up and gather itself along the length of tube 32.

The ring 36 is silicone completely enclosing the semi-flexible chain ring 37 that fits snugly into the pyloric portion of the stomach. (The chain used in the ring is not interrupted.) The ring 36 is large and strong enough in the non-flexible dimension of chain 37 so that it braces itself against the stomach wall and does not pass the sphincter. It is sufficiently flexible in another dimension to be compressed within the catheter during insertion and removal. The shape of the retaining ring is such that it moves with and adapts to both the stomach's contour and peristaltic contractions. The top and bottom silicone walls of ring 36 are of a sufficient thickness and elasticity so that ring springs back into an open position after each peristaltic contraction while fully conforming with each contraction.

The loop 28 hangs about halfway into the lumen of ring 36. This loop 28 has a magnetic property. In greater detail, the loop 28 may be a silicone tube approximately 0.025 inches in diameter and ½ inch in length. Enclosed within the tube of loop 28 are tiny segments of magnetically attracted material, such as a magnetic plastic material or steel. Preferably, this magnetic material is opaque to X-rays so that it may be recognizable under a fluoroscope. The two ends of the loop are attached to the turnable tube 29 which fits somewhat loosely around a straight section in the chain 37 embedded in the ring 36, so that the loop (and, therefore, ring 36) may be captured and deflected from its normal position responsive to a magnetically attracted material on the end of the catheter. When a connection is made between the magnets 82,84 and the loop 28, the free end of loop 28 may be drawn into and enter the catheter. The ring 36 is also drawn in and compressed behind the loop for both insertion into and removal from the body. Therefore, it is preferable for the chain 37 and the loop 28 to have an even number of uniformly spaced links 46 or magnetic segments 49, respectively. Thus, upon compression, there is a precise fold with each link aligned with a corresponding link on the opposite side of the ring or loop.

Figure 4:
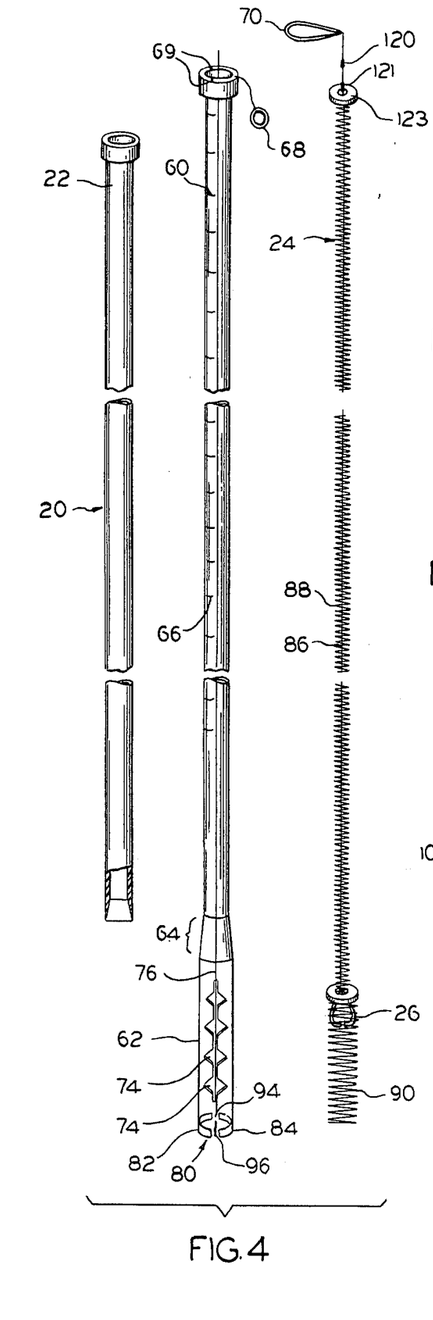
FIG. 4 is a perspective view of each of the three main parts of the catheter which is used as a tool for implanting and removing the tube of FIG. 2.

The catheter 20 of FIG. 4 is used when the tubular implant 30 is inserted or implanted in the small intestine, and when it is later removed therefrom, without an operation. A knowledgeable doctor may be able to insert and remove the implant without the use of a fluoroscope, because magnets 82,84 perform an alignment function without requiring precise human guidance.

In general, this catheter 20 comprises three coaxial, tubular members, which are separately shown in FIG. 4. The outside tubular member is sheath 22. The intermediate tubular is inner tube 60. The innermost tubular member is the tool 24. The sheath 22 and inner tube 60 are telescopingly fitted together to vary the effective length of the catheter in order to conform to a patient's stature. In effect, the sheath 22 functions as a lining for the mouth, pharynx, and esophagus so that the tool running through it may be manipulated without directly rubbing or irritating these and similar body parts.

In greater detail, the inner tube 60 is a longer and thinner diameter tube, which fits inside the shorter and slightly wider diameter sheath 22. The inner tube 60 may be about 28" long, including a handle portion. The sheath 22 may be about 22⅝" long, including a handle. The outside diameter of the inner tube 60 should be about 2 mm less than the inside diameter of the sheath 22 for maneuverability. The preferred measurements for these parts are approximately:

| Inner Tube 60 | Sheath 22 |
|---|---|
| 4 mm I.D. | 7 mm I.D. |
| 5 mm O.D. | 9 mm O.D. |

Approximately, the bottom four inches 62 of the inner tube 60 widens to become an outside diameter of approximately 7 to 9 mm, which is about the same as the outside diameter of sheath 22. Therefore, the two tubes appear to the digestive tract as one continuous catheter of substantially the same outside diameter.

Figures 5, 6A, 6B, 7, 8:
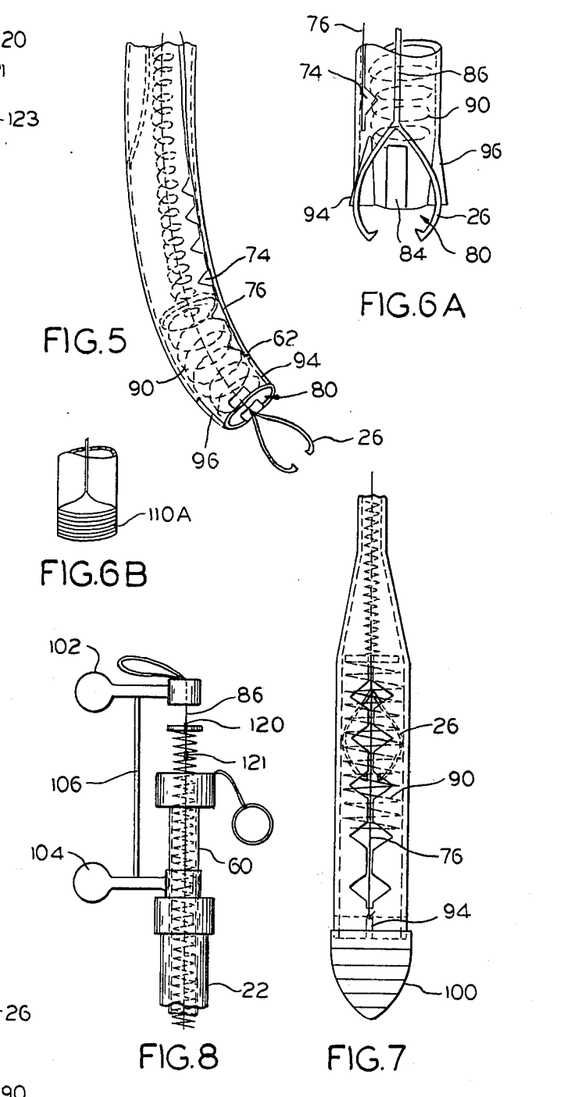
FIG. 5 shows the device at the end of the catheter for controlling the degree of curl in the lower section of the catheter as it is used for insertion and removal of the implant.
FIG. 6A pictorially shows how tweezers are oriented and extended from the inner tube of the catheter.
FIG. 6B shows an alternative capture means in the form of an electromagnet.
FIG. 7 shows, by way of example, the inventive catheter, after it has been prepared for insertion into the stomach preparatory to a retrieval of the implanted tube.
FIG. 8 shows a safety guard which may be used to secure the parts of the catheter in place during insertion and removal of the implant in FIG. 2.

The considerations for these measurements are that the inner tube 60 should have the smallest inside diameter that may contain a workable tool 24 or an alternate means, such as an electromagnet seen in FIG. 6B. The walls of the inner tube should be about ½ mm thick, for currently available materials. The taper 64 of the widening portion 62 of the inner tube 60 should occur within about one inch of catheter length. This one-inch length is selected since it is long enough for a gradual change and not too long to interfere with the performances of the tool. The bottom three inches 62 of inner tube 60 should have an inside diameter which is large enough to receive the loop 28 and compressed stomach ring 36. Also, the walls of section 62 should be strong enough to contain and withstand the pressure caused by this compression of ring 36.

The length of inner tube 60 is marked at 66 in centimeters or inches, starting about 10" from the bottom of the catheter and ascending to the top so that the total usable length of the catheter is easily known when parts 22,60 are telescoped together. Preferably, these numbers are upside down on one side, relative to the numbers on the other side, so that the telescoped length may be easily read, regardless of the catheter's position when read.

A pair of handles 68,70 are associated with the inner tube 60 for manipulating the catheter. In greater detail, the lower and enlarged end 62 of the inner tube 60, has a series of semi-circumferential wedge or V-slots 74 (FIG. 5) cut therein perpendicular to the axis of the tube and covered with a thin layer of silicone or other desirable material. A cord 76 runs down a passageway in the tube wall, extending almost the entire length of the inner tube 60. The cord passageway ends about ⅜-½ of an inch from end 80 of the inner tube, before slit 94 (FIG. 6A) begins. The cord 76 extends loosely through notches 74 and is attached at the lower end of inner tube 60 to the passageway through which cord 76 passes. Therefore, when the cord 76 is pulled, by means of an extending handle 68, the V-notches tend to close, thereby curling the inner tube over a radius which is variable, depending upon the tension in cord 76. This curling enables the end 80 of the inner tube to be pointed in a particular direction. Hence, by pulling the cord a discrete distance and by rotating the inner tube 60, within sheath 22, the end 80 may be guided through the stomach and toward the pyloric portion of the stomach.

Two diametrically opposing crescent-shaped magnets are secured on opposite sides of the inner tube 60, at the end 80. The magnets are spaced evenly, each extending over about one-fourth to one-third of the total circumference of the inner tube 80. The magnets are preferably covered by a very thin layer of silicone or other material to prevent any interaction between the magnetic material and body chemistry. Preferably, the magnets are opaque to X-rays so that they may be guided through use of a fluoroscope.

Inside the inner tube 60 is the tool 24 which includes a cord or wire 86 extending through a flexible wall stiffener 88. At the bottom of the tool 24, the wall stiffening material has a larger diameter 90 for fitting within and reinforcing the enlarged area 62 of the inner tube. The elements 88,90 may be thought of as a coiled spring made of plastic or other material. The wire 86 is marked with two or more color-coded bands 120,121 which aid a doctor who may not wish to use a fluoroscope. A combination of correlated sizes makes it possible for the doctor to tell if loop 28 and ring 36 are properly compressed inside the catheter 62 prior to removal of implant.

Inside the large area 90, tweezers 26 are secured to the bottom of the cord or wire 86. Preferably, when closed, these tweezers are substantially the same size as the inside diameter of section 90. They spring out under their own spring bias to open and become wider than this inside diameter of section 90 when they are pushed out of the end 90 of spring reinforcement 88. They close securely when they are pulled into the end 90. When the tweezers are extending from end 90 but still within catheter 80, the prongs are not open sufficiently to embrace loop 28. Therefore, additional width is needed to open the tweezers to the correct span while they are being extended past end 80. The slits 94,96 are formed in inner tube 60 and allow the tweezers to open wider and thereby adjust the tweezers' width sufficiently to grasp loop 28.

As best seen in FIG. 6A, the bottom end of the inner tube 60 is slit at 94,96 for a distance of about ¼", up the side, slit 94 beginning after the end of the cord lumen. These slits are in the area between the semicircular magnets 82,84. The slits are normally held closed by the resilience of the tube 60, unless the tweezer's prongs push out through them, thereby causing each slit to open approximately 2 mm before their covering becomes taut, preventing further opening. The tweezers' prongs may be positioned by aligning the oval handle 70 above a colored strip 69 on the handle of inner tube 60. When aligned, the prongs are in the correct position to grasp the loop 28 when the tweezers are extended. Therefore, the slits enable the tweezers' prongs to open wider than they otherwise could open inside the catheter 80 to reliably encircle the loop 28. Also, since the tweezers are bowed to push outwardly, they move stomach folds out of the tweezers' reach.

Since the spring bias of the tweezers' prongs opens them as they are pushed out of spring 90 and into the slits in the catheter, this procedure of opening the tweezers may be followed to release the loop 28 when the tube 32 is implanted. To remove the implanted tube, the tweezers are pushed out to open. The position of the tweezers' prongs may be manipulated by pulling cord 76 to curl the end of the inner tube 60 as it approaches the loop 28. The magnets 82,84 attract the magnetic material in the loop 28 as it is so attracted. To further assist in indexing the rotational position of the tweezers, the oval ring 70 may be turned to correspond with the location of stripes 69 printed on the inner tube handle.

In operation during implant removal, a connection is made between the catheter end 80 and the loop 28. The free end of loop 28 is drawn against the magnetic material 82,84 on the end of the catheter 80. To check for a connection between the magnet and loop 28, move inner tube 60 up and down. If resistance is felt, the loop is connected to the magnets. If so, position tweezers 26 and push them out of catheter 80 to grasp loop 28. Hold the disk 123 against a wall reinforcement at the upper end of the inner tube 60. This causes section 90 to align with end 80 to close the tweezers as they are pulled slightly into section 90. Pull up handle 70, bringing the tweezers (loop 28 attached) into section 90. Ring 36 collapses behind loop into catheter 62. Ring 36 pushes section 90 upwardly as it is compressed into section 62. The ring and loop are compressed when a colored band 120 aligns with an extending disk on the reinforcement wall at the upper end of the inner tube 60.

The electromagnet 110A of FIG. 6B is situated within the distal circumference at the end of the inner tube 60 of catheter 20. The tweezers 26 and the spring reinforcement tube 88 may or may not be used in conjunction with the electromagnet. If the tweezers 26 and the spring reinforcement tube 88 are used in conjunction with electromagnet 110A, they may be made of a plastic material so as not to be attracted to the electromagnet.

Prior to retrieval of the tube 32, the catheter is prepared for insertion down the patient's throat and into the stomach. A slow-dissolving gelatin capsule 100 (FIG. 7) is placed in the end of inner tube 80 to streamline it and prevent it from snagging on the way down the throat. Once the catheter reaches the stomach, the handle 70 is pushed and the gelatin capsule is dislodged into the stomach where it slowly dissolves. The end 80 of the catheter is then turned and tensioned by cord 76 to curl (FIG. 5) so that the magnets 82,84 approach loop 28, the connection being seen in FIG. 1.

FIG. 8 shows a safety guard which may be used to secure the catheter parts for insertion into or removal from the patient's body. This safety guard comprises two spring-loaded clamps 102,104 rigidly secured together by a rod 106. Therefore, the clamp 102 may be attached around wire 86 and the clamp 104 may be attached around the inner tube 60. This means that there is no way for the tweezers 26 to inadvertently slip out of the large part 62,90 of the catheter during insertion or removal. The two tubes 22,60 are telescoped together at a point in section 64. During implantation, once the tube 32 (FIG. 1) is properly lodged in the intestine during insertion, the guard clamps 102,104 are removed to manipulate catheter. During removal, the guard is attached after the stomach ring is securely captured in the large part 62 of the catheter. The length of the safety guard corresponds to the distance needed to compress the implant loop 28 and ring 36. The remainder of the implant tube 32 retains a compressed form when empty of food.

Two colored marks 120,121 may be formed on the wire 86. When handle 70 is pulled while the tweezers 26 have a grip upon loop 28, the ring 36 is captured and pulled into the catheter end 62 far enough so that mark 120 may be seen above the disk 123. However, if the tweezers do not have a grip upon loop 28, the handle 70 may be pulled further and the mark 121 will be seen above the disk 123. Conveniently, these marks 120,121 may be color-coded for easy identification.

Other uses for the catheter might include removal of foreign objects from the body of a patient—especially, although not exclusively—removal of foreign objects from the digestive tract of a person. Many times, foreign objects may become lodged or caught in the pharynx, esophagus, or stomach. Such objects may include bones, pins, coins, wires, and the like. For example, small children have been known to swallow pins and anyone may accidentally swallow bones while eating fish, chicken or other foods with small bones. When a person swallows such potentially dangerous objects, surgery is often required for their removal. Catheter 20 in FIG. 4 or one of the electromagnetic catheters (such as shown in FIG. 6B) may be used either separately or together for removal of objects from the body. The permanent magnets 82,84 may attract magnetic material objects and the tweezers 26 may be extended to bring an object safely into the catheter end 62 prior to its removal from the digestive tract.

An alternate means for capturing and pulling a magnetic material object into the end of the catheter uses a magnetic means attached to the end of an elongated spring or similar instrument which extends through inside the lumen of inner tube 60 and into the stomach area.

Catheter 20 of FIG. 4 may also be used for removal of non-metallic objects from the body in conjunction with a fluroscope or other visual detecting machine. The catheter 20 is inserted and guided to the foreign body by a continuous inspection of a fluoroscope. Then, end 80 of inner tube 60 is maneuvered and tweezers 26 grasp the object.

To aid in visual location of objects, the catheter may have a light located on or near its lower end. For example, FIG. 11A shows a bundle of optical fibers 85 lit by a lamp 89 which is outside the catheter. The lower end of optical fibers 85 may be projected out of the lower end of inner tube 60.

The catheter may also be used to insert and remove implants (FIG. 10) which restrict absorption in portions of the alimentary canal. Implant instrument 218 has several modifications as compared to the tubular implant 30 of FIG. 2. For example, implant instrument 218 includes a narrow, elongated spring device 220 which has a length 230 calculated to bypass the pylorus and the common bile and pancreatic ducts. An advantage to such a bypass is that it better enables the enterogastric reflex which controls the rate at which the stomach empties its contents. That rate is determined by the amount of fat which is present in the duodenum. Another advantage for bypassing the bile and pancreatic ducts is to prevent any possibility that the tubular lining might block the ducts. Furthermore, the longitudinal give of the spring 220 either eliminates or greatly reduces the amount of peristaltic pull which acts through tube 228 and onto that portion of the alimentary canal which contains the means for anchoring the implant.

Another modification of the implant instrument 218 includes an alternative anchoring means, which is represented in FIG. 10 as a relatively narrow, somewhat crescent-shaped or bar-type device 224. An advantage to this type of anchoring means is that it comes into contact with a smaller area of the alimentary canal as compared to the contact area of ring 36, thereby reducing the area of possible erosion of the pyloric part of the stomach.

For example, crescent anchor means 224 may be a thick silicone encasement surrounding a section of semi-flexible chain similar to that shown in FIG. 3. The chain is flexible when pulled toward the pyloric muscle; yet it does not pass through the muscle since the center link 234 of the chain 232 is too wide to pass. Incorporated into one end of crescent anchor means 224 is a metallic tab 236 which may be attracted by an electromagnet during an insertion into or a removal from the body. The elongated spring device 220 is attached to the back of crescent anchor means 224, in the middle of center link 234. When the tab end 236 is pulled, the crescent shape 224 straightens and aligns itself with the spring 220 so that it may pass into the catheter tube 60.

Still another modification of implant instrument 218 replaces the semi-flexible support chain 34 with a flexible, flat spring 226. Support spring 226 gives the implanted tube greater flexibility, yet retains enough support to prevent it from twisting responsive to the movements within the alimentary canal.

Spring 226 is loosely wound, preferably either covered with silicone or situated within a gathered silicone encasement tube. Spring 226 readily elongates or contracts in its longitudinal dimension responsive to the peristaltic movements in the gastrointestinal tract which are acting upon the implant tube 228. Thus, when the gentle peristaltic movement pulls on tube 228, the springs 220,226 elongate. When the peristalsis acting on tube 228 relaxes, springs 220,226 contract, thereby isolating the pull of peristalsis from the crescent anchor means 224. Spring 220 extends a predetermined distance and then branches into a plurality of separate spring sections, such as 238,240, for example. These spring sections are attached to opposite sides of a contour ring 242 which forms the beginning of the balloon-like tube 228. These branch springs hold the end ring 242 substantially perpendicular to the intestine so that food solids will enter it.

Support spring 226 is preferably embedded within the walls of tube 228 while in a slightly elongated state, which will cause the tube to be slightly gathered in its relaxed state. This gathering will enable the tube to better follow the intestinal movements.

The contour ring 242 is here shown as if it were transparent so that its internal construction may be seen. Preferably that construction enables it to expand or contract in order to more nearly conform to the dimensions of the surrounding gastrointestinal tract. In greater detail, ring 242 has a generally spiral, double lumen passageway 249 in which ends 250,252 of a drawstring or spring strip 254 slide. End 250 may slide a predetermined distance into passageway 249 before being stopped by a wall 258, and end 252 of strip 254 may slide a predetermined distance into passageway 249 before being stopped by a wall 256. The walls of the passageway extend around approximately one half of the circumference of contour ring 242 and are made of a generally stiff, yet flexible, material. Encircling the other half of ring 242 is a gathered silicone encasement tube 260, in which strip 254 is situated. Thus, when ring 242 contracts, the encasement tube 260 gathers. When ring 242 expands, the encasement tube 260, surrounding strip 254 expands. The balloon-thin tube 228 is attached around the circumference of contour ring 242; thus, when the contour ring contracts, the tube 228 tends to gather slightly around the ring.

In operation, when the surrounding intestinal pressure on ring 242 causes it to compress, ends 250,252 of strip 254 slide through the passageways. When the intestinal pressure on ring 242 relaxes, strip 254 opens somewhat under its own spring-bias, drawing ends 250,252 toward their respective wall openings. However, their protruding or mushroom end portions prevent them from passing through the openings in the walls.

Incorporated into the end of wall 256 within contour ring 242 is a magnetically attracted material 262 which may be used to attract the ring 242 as it is drawn into a catheter. The material 262 is situated within the outer side of the contour ring 242 near the point where the gathered silicone tube 260 joins the semi-flexible track passageways 249. During insertion and removal of implant 218, the electromagnetic catheter 110A attracts the material 262 so that the contour ring 242 may be pulled lengthwise into the catheter, thus compressing ring 242 into a suitable reduced size for insertion into and removal from the body.

An alternative structure 270 for an electromagnetic catheter is shown in FIG. 11. The electromagnetic catheter 270 combines features of the catheter 20 of FIG. 4 with the electromagnet of FIG. 6B. It also replaces the tweezers 26 with a new form of grasping device 272 which may be opened and closed without being pulled into and out of a confining tube.

In greater detail, catheter 270 includes two members. The first member comprises a long tube 274 which has one uniform diameter. The second member comprises an elongated grasping device 272 with a tweezers-like tool 276 incorporated on its lower end. Grasping device 272 runs throughout the length of and within the lumen of tube 274. This tool 276 may be used to pull tab 236 (FIG. 10) of crescent 224 into the lower end of catheter 270 once the metallic tab is captured by the electromagnet 278 secured around the circumference and within the walls at the end portion of tube 274. The electromagnet 278 is energized by way of a wire running within the walls of tube 274 and leading to any suitable plug 280. The end portion 282 of tube 274 may be curled to the desired angle as taught at 62 (FIG. 4). The V-slots may be formed on several sides of tube 274 and the cord 76 may be duplicated for each series of slots to curl the tube in several desired directions.

An alternate means for curling the end portion 282 of the catheter 270 is to incorporate a spring guide in the tube 274. This spring guide is similar to guides which are inserted into a tube and used in the vascular system for guiding and angling the end of a tube into and through the various branches of blood vessels. Such a spring guide comprises a spring section through which wires or rods loosely run. The wires or rods are secured to the end of the spring section. In operation, a desired wire is pulled and the spring section curls in the desired direction, thereby curling the tube.

Grasping device 272 extends through the lumen of tube 274. In greater detail, two separate elongated members 288,290 run vertically and generally parallel to each other. At the lower end portions, the members 288,290 cross each other to form the opposed members of a tweezers-like tool 276. Members 288,290 of the grasping device are held together by two tensioned springs 292,294 which are situated near their intersection. A pair of handle portions 296 are formed on the outer end for opening and closing the tweezers-like tool. Color-coded bands 300,302 may be formed at selected locations on the grasped device to aid a doctor during insertion and removal of an implant instrument.

Prior to insertion of the implant into the body, the electromagnet 278 (FIG. 11) is energized and tab 236 (FIG. 10) of crescent anchor means 224 is placed on its end. Grasping device 272 grasps and pulls both tab 236 and the crescent anchor means 224 lengthwise into the lumen of tube 274. The grasping device is pulled far enough to pull the ring 242 into the catheter. As the separate spring sections 238,240 (FIG. 10) begin to enter the catheter, they are drawn together, thereby drawing the opposite sides of contour ring 242 together. Electromagnet 278 attracts the magnet 262 on the outer side of the contour ring. The contour ring 242 is pulled lengthwise into the catheter end 282. When the contour ring 242 is compressed inside the catheter, a color-coded band 300 on the grasping device is aligned with the catheter handle 298. When the end of the catheter is in the duodenum, the electromagnet 278 is turned off and the grasping device 272 pushed downwardly to release the contour ring 242 which is now out of the catheter and into the duodenum.

An alternate means for compressing the contour ring 242 is to magnetically attract ends 250,252 (FIG. 10) of strip 254, thus pulling them and greatly reducing the outer diameter of contour ring 242.

For removal of implant instrument 218 from the body, the catheter 270 is prepared for insertion into the body with a slow-dissolving streamlined gelatin capsule 100 attached on end 286 to streamline the catheter for its entry into the body. When the catheter is inserted approximately 20-25 inches into the body, the end 286 is within the stomach. The electromagnet 278 may be energized and the grasping device 272 extended to dislodge the gelatin capsule 100 from the end of catheter 270. The end portion 282 of the catheter is then curled to point in the desired direction for the electromagnet 278 to attract and capture tab 236 of crescent anchor means 224. Grasping device 272 is then pushed down and the tweezer-like tool 276 is opened to grasp and pull the tab 236. The anchoring means 224 straightens and moves into the catheter 270. The grasping device 272 is pulled upwardly until color-coded band 300 is visible above the catheter handle 298, which means that the contour ring 242 is compressed within the lumen of the catheter 270.

An alternative embodiment 320 (FIG. 12) of the implant instrument controls absorption in only limited portions of the alimentary canal. The implant instrument 320 has a series of balloon-like tubes 322,324, each of which is similar to but much shorter than the tubes 32,228. It further replaces the expandable spring section 220 (FIG. 10) with a form of extendable device including a spring-loaded tensioned reel 326, within a crescent anchor means 328. Cord 330 is wound or unwound by the pull of the gastrointestinal peristalsis acting against the spring of reel 326.

Figures 12, 12A, 12B, 13, 14, 15, 16:
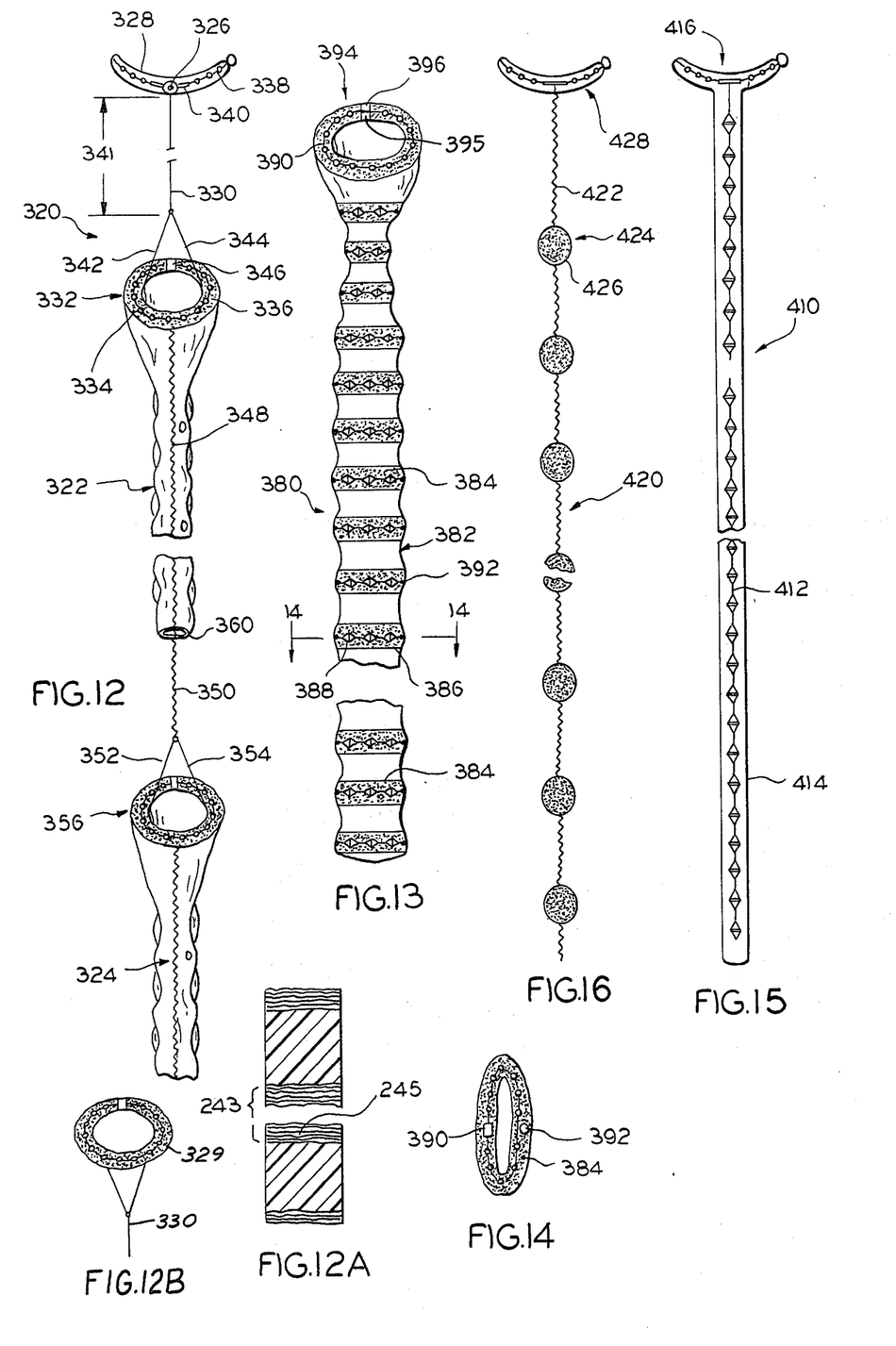
FIG. 12 schematically shows, somewhat in perspective, an interrupted implant instrument comprising several separate, but interconnected, balloon-like tubes for lining some portions of the alimentary canal, while bypassing other portions from a tubular lining.
FIG. 12A shows an alternative structure for providing an interrupted tube.
FIG. 12B shows an alternative ring shaped anchor means.
FIG. 13 shows a balloon-like tube which includes a series of magnetically compressed rings, which provide an artificial peristalsis.
FIG. 14 is a cross section taken along line 14—14 of FIG. 13 showing an artificial peristalsis contraction.
FIG. 15 shows, somewhat in perspective, a long section of the semi-flexible chain within an encasement tube which may be used alone for stimulating and increasing absorption in the intestinal tract.
FIG. 16 shows an elongated implant instrument with crushable bulges distributed along its length for stimulating absorption only in desired portions of the intestinal tract.

The instrument 320 may be implanted into the gastrointestinal canal for restricting absorption only in desired areas, while not restricting absorption in other areas. This embodiment may be desired for a number of reasons such as to treat an illness (such as an ulcer) at a given point or to enable absorption at some points while denying it at other points.

Still another alteration in the embodiment 320 is a different type of contour ring 332 which includes a section of the semi-flexible chain 334 (similar to the chain of FIG. 3) which is covered with a soft, pliable sponge 336 secured around its outer circumference.

In greater detail, crescent anchor means 328 contains a section of the two-dimensional chain 338 (FIG. 12) or ring shaped anchor means (FIG. 12B) may be a ring similar to rings 336 or 356 (FIG. 12).

The chain is flexible when pulled toward the pyloric muscle, yet it does not pass through the muscle since center link 340 of chain 338 is too wide to pass therethrough. Incorporated in the middle of center link 340 is the tensioned reel 326 around which cord 330 is wound. Thus, when the gentle peristaltic movement pulls on implant instrument 320, cord 330 unwinds from reel and simultaneously winds a clock spring (not shown) inside the reel. When the intestinal peristalsis relaxes, cord 330 rewinds into reel responsive to the energy stored in the clock spring, thereby keeping most of the pull off the crescent anchor means 328.

Cord 330 extends a predetermined distance 341 before branching into at least two cord sections 342,344.

Cord sections 342,344 are attached to the semi-flexible contour ring 332. The diameter of the ring is approximately the same as the diameter of the duodenum or of another intestinal portion, in which it may be situated. The sponge 336 encircling the semi-flexible chain ring 334 molds itself to the dimensions of the surrounding intestinal tract. Securely positioned within the outer side of the contour ring is a magnet 346 which may be used to attract the ring and draw it into the catheter during removal of the implant 320.

Attached to the back of contour ring 332 is a balloon-like tube 322, of a desired length. Tube 322 is stabilized by a flat spring section 348 which runs lengthwise and is embedded within the walls of tube 322. Tube 322 is joined to the next balloon-like tube 324 by means of a continuing section 350 of the support spring 348. This section 350 of the support spring may also be encased within an expandable, gathered silicone tube so that the spring section 350 presents a smooth surface to the surrounding body tissues. The support spring section 350 may be replaced with reel device similar to reel 326. Spring section 350 extends a desired length before branching into cord sections 352,354 which are attached on opposite sides to the next semi-flexible contour ring 356 and its associated balloon-like tube 324. Any number of tube sections may be joined together in a similar manner.

The food chemicals will leave the first tube 322 at its end 360, and be absorbed in natural amounts in the area of the spring section 350. Thereafter, the food chemicals enter into the next tube 324, which again restricts absorption.

Implant instrument 320 may be inserted into and removed from the body by catheter of FIG. 12, as described in connection with FIG. 10.

The implant tubes of FIGS. 2, 10, 12 and 12A and B have all been described as beginning and being anchored in the pyloric portion of the stomach. However, other sphincter muscles also provide possible holding and anchoring points, such as the duodeno-jejunal flexure which connects the duodenum and jejunum, the ileo-caecal valve which connects the small and large intestine, or the internal sphincter muscle in the rectum. For example, if a patient needed to have a restricted absorption of food or body chemicals in the lower portion of the small intestine or large intestine, an implanted tube could be inserted through the rectum (anchoring means last) and its anchoring means could rest against the ileo-caecal valve or internal sphincter muscle in the rectum. The balloon-like tube would travel up from its anchor means, through the large intestine and, if desired, into the small intestine.

For this use, the uppermost end of the implanted balloon-like tube is held open, for digesting food chemicals to enter, with one of the contour-type rings (similar to the contour ring 242 of FIG. 10, for example). When the implant is inserted and positioned in the desired part of the intestinal tract, it is necessary to counteract the downwardly acting peristaltic movement. To counteract this downward peristalsis, a semi-rigid rod or wire may be inserted through an opening in the anchoring means and from the anchoring means through the balloon-like tube. For example, a semi-rigid rod or wire is easily inserted through the encasement tube which is described above as surrounding the semi-flexible chain or the enclosed spring sections.

Still another modification for the implant tubes of FIGS. 2, 10 and 12 is to make the balloon-like tubes more porous, in desired areas. For this, the balloon-like tubes could be formed into a mesh-type material 243 (FIG. 12A), which would have numerous perforations, for enabling a less restricted absorption of food chemicals. If the mesh is then impregnated periodically, as at 245, there is an interrupted tube, similar to the one shown in FIG. 12.

A further modification in the implant tubes is to have large lengthwise openings formed along portions of the balloon-like tubes for enabling a greater absorption of food chemicals and for bypassing the tube around the common bile and pancreatic ducts.

Yet another modification includes further improvements in the means for anchoring the implant tubes of FIGS. 2, 10, 12 and 13 or altering the support structures which stablize the balloon-like tubes. For example, the means for anchoring the implant tubes could be made in the form of an airtight float which would tend to draw the anchoring means slightly upward in the fluid, which is present in the pyloric portion of the stomach. To make such a float, the sponge material in the anchor ring 394 (FIG. 13) is a cellular material filled with small air bubbles which do not communicate with each other or with the surrounding fluid. A floating-type anchor means has an advantage since it eliminates or reduces erosion on the stomach walls. Also, the means for supporting the balloon-like tubes could be altered. For example, a slender, flexible, folded leaf spring or rod lengthens and contracts, relative to the gastrointestinal movements, while preventing the balloon-like tubes from twisting.

Still another modification encircles a balloon-like tube 380 (FIG. 13) with a series of the magnetically compressed contour rings. Each such ring may be individually controlled to magnetically compress and expand to create an artificial peristalsis for passing food chemicals through the tube.

In greater detail, the implant instrument 380 includes a long balloon-like tube 382 which is lined periodically with a series of semi-flexible, sponge-covered contour rings 384. Each of these contour rings 384 is formed of a semi-flexible chain ring 386 which is covered around its outer circumference with a soft, supple sponge material 388. The rings are preferably encased with a silicone covering. The contour rings are flexible in the radial direction and yet retain their open shape from the memory of the plastic forming the sponge covering silicone encasement. The contour rings 384 are spaced approximately one-half inch apart continuously throughout the entire length of the tube. Secured within each contour ring 384 is a metallic fixture 390 which is periodically drawn toward a small electromagnet 392 situated on the opposite side of the ring. A suitable self-interrupting circuit 395 may be provided to periodically interrupt a battery circuit. The battery pack 396 may be similar to those used for implanted pacemakers.

In operation, a magnetic field is created by the electromagnets 392 in each ring. The metallic fixtures 390 are drawn toward the electromagnets, thereby tending to compress each contour ring as shown in FIG. 14. The battery is timed to interrupt its circuit periodically for causing the various rings to simulate peristalsis. Each time that a circuit is interrupted, the plastic memory returns the ring to its original open shape. Thus, the food chemicals are slowly squeezed through tube 382 by the expanding and contracting of the contour rings 384. The implant instrument 380 for artificial peristalsis may be inserted and removed with any of the above-described catheters.

FIG. 15 shows a long section of the semi-flexible chain in an encasement tube, much like as shown in FIGS. 3A and 3B. This chain may be used alone, without the balloon-like tube, for stimulating and increasing absorption in the adjacent intestinal tract. In greater detail, the bulk control instrument 410 of FIG. 15 includes a section of the interrupted, two-dimensional chain 412 which is encased in a closed tube 414. Attached to one end of encasement tube 414 is a crescent-shaped anchoring means 416.

The encasement tube 414 for the bulk control instrument 410 may be approximately one-quarter to one-third inch wide, thus adding substantial bulk to the intestine. The bulk control instrument stimulates and increases the intestinal peristaltic squeezing contractions for causing added absorption of food chemicals. The encasement tube further acts as an obstacle to retard the transport of food chemicals through the intestine—thus causing more absorption into the villi.

Basically, there are two types of peristaltic movements which occur with varying intensities within the digestive tract. One is a concentrated squeezing contraction which causes the absorption of food chemicals. The other is a wave-type of movement which transports the food chemicals through the digestive tract. As the food chyme enters the duodenum, there is a concentrated squeezing contraction which can last for periods extending from 15 seconds to over a minute, depending on the location and on the intensity of the squeezing contraction. Then, a wave-type of peristaltic movement pushes the food from that section of the intestine onto the next section, where the concentrated squeezing contraction begins again, and so forth.

Studies reported by Meyer O. Cantor in his book, *Intestinal Intubation,* show that if bulk, such as a tube, is present in the intestine, the tube stimulates the intestinal muscles into producing more and longer peristaltic squeezing contractions. Thus, more absorption takes place in the area where the squeezing lasts longer than would ordinarily occur. This increase of absorption within the human body is substantiated by a study of the causes of constipation, which results when food solids remain with the large intestine for longer than natural periods of time. If the food solids remain in the large intestine longer than they should, they stimulate excessive osmosis in the large intestine, thereby removing too much fluid from the food solids which results in constipation. This excessive osmosis carries with it an increase in food absorption.

Another factor for determining the amount of absorption into the villi, if any given area of the intestine, is the density and length of the valvulae conniventes as folds present in that area of the intestine. The valvulae conniventes are folds which extend into the lumen of the intestines to retard the passage of food at that point and to provide a more extensive surface for absorption. Therefore, the amount of absorption into the villi, in any given area of the intestine is basically dependent upon two factors: the intensity and duration of the peristaltic squeezing contractions in that area and the density and length of the valvulae conniventes or folds present in that area.

The bulk control instrument 410 takes into account both of these factors by stimulating and increasing the peristaltic squeezing contractions while slowing the transport of food chemicals. Furthermore, the bulk control instrument also causes the intestinal villi to increase in size since they are used more for absorption. When the implant 410 is removed after a period of time, the larger villi and their larger openings cause still more absorption of food chemicals to occur, at least for a limited period of time.

The encasement tube 414 may be shaped or billowed, into a wider diameter in desired areas, where greater absorption is desired.

An alternate embodiment for an implant which stimulates absorption is shown in FIG. 16. Implant 420 includes a long, encased spring section 422 interconnecting a plurality of crushable sponge balls or bulges 424 encased within a silicone covering 426. The balls are positioned to coincide with the intestinal area in which additional absorption is desired. The positions of the balls may be changed so that a doctor may tailor the insert to the needs of a particular patient. The bulk control instrument 420 may thus be used for stimulating absorption in only the desired areas of the intestinal tract.

The bulk control instruments of FIGS. 15 and 16 may be used for treating certain dietary deficiencies, chronic diarrhea, or for stimulating peristalsis in persons who have weak, sluggish intestinal tracts, and the like. Any one of the previously described catheters may be used to insert and remove the bulk control instruments for stimulating absorption.

Those who are skilled in the art will readily perceive still other changes and modifications which may be made in the inventive structures and perceive new and different uses for the inventive structures. Therefore, the appended claims are to be construed broadly enough to cover all equivalent structures falling within the scope and the spirit of this invention.

I claim:

1. A method of inserting an instrument including a thin wall tube which is open on both ends and is implanted while completely empty and collapsed in radial dimension, said tube comprising means for restricting absorption of food chemicals within at least the intestinal portion of the alimentary canal of an animal body while said food chemicals are being squeezed by bodily peristaltic action, said method comprising the steps of (a) inserting a thin wall tube while in a state which is flexible enough to be passed completely through the throat and be implanted entirely within said portion of said alimentary canal which is below the stomach at a position wherein said tube does not extend out of the intestinal portion of the alimentary canal of said body while it is so implanted, said tube lacking substantially all radial rigidity and being completely collapsible at least in parts when empty and at the time of implanting, (b) locating said tube with its open ends positioned to enable digesting food chemicals to enter and expand said tube only to the extent that food is within said tube and to pass under peristaltic action completely through said tube while digestion continues whereby said tube may be used to control absorption of food chemicals in that portion of the alimentary canal which is lined by said tube, said digesting food chemicals which pass through said tube being the normally consumed food which enters the body in whole, non-digested form through the mouth of a patient, said non-digested food solids becoming partially digested in the stomach before coming into contact with and entering said implanted tube, and (c) anchoring said implant tube at a point which is below the intake to the stomach so that said implanted tube and its entire anchoring remain in place entirely within a selected part of the alimentary canal, below said intake point.

2. The method of claim 1 wherein said implant tube is an extruded tube.

3. The method of claim 1 wherein said implant tube is a molded casting.

4. The method of claim 1 wherein said tube means has longitudinal folds which reduce its effective diameter when empty of said food chemicals, said longitudinal folds opening outwardly to increase the effective diameter of said tube when said tube is filled with food chemicals.

5. The method of claim 1 wherein said tube is formed to billow and constrict generally following the naturally-occurring shape of the interior of a small intestine.

6. The method of claim 1 wherein said anchoring of said implant tube includes an impervious, airtight float which is capable of floating in the stomach.

7. The method of claim 1 wherein interrupted portions of said walls of said open-ended tube are formed by a porous mesh-type material.

8. The method of claim 1 wherein extended longitudinal portions of the wall of said tube are open.

9. The method of claim 1 wherein said open-ended tube is a balloon-like tube which has an elongated semi-flexible support means running lengthwise within said tube to prevent it from twisting responsive to peristaltic movements acting upon said tube when implanted within said alimentary canal, and semi-flexible ring means around the circumference of one of said open ends to hold open said one end so that digesting food chemicals enter into said tube.

10. The method of claim 9 and the step wherein said semi-flexible ring is surgically bound in place within the body of a patient so that said balloon-like tube does not pass from that portion of the alimentary canal in which it is anchored.

11. The method of claim 9 wherein said open-ended, balloon-like tube is supported by a hollow, elongated, semi-flexible, tubular means running lengthwise within said balloon-like tube, whereby an elongated semi-rigid rod or wire may be inserted through said hollow, semi-flexible, tubular means to give a more rigid support to said semi-flexible means.

12. The method of claim 1 and the step of punching holes along said tube implant means, said punching being made by a two-member, scissor-like instrument which has a protruding punch on one member and a mating die on the other member.

13. The method of claim 12 wherein said punch and die are oval.

14. The method of claim 1 wherein the walls of said tube means are reinforced by strips of material attached to and running lengthwise within the walls of said tube.

15. The method of claim 14 wherein said reinforcing means are strands of catgut.

16. The method of claim 1 and said step (a) using means for inserting and removing said implant means in a patient's body, said insertion means comprising a catheter having means for capturing and holding at least an end of said tube while it is being inserted or removed and for releasing said tube after it is implanted, whereby said catheter may be removed while the tube remains in place, said catheter having means for curling its end in order to approach the end of said tube, the ends of said tube and of said catheters having complementary coupling means for seizing the tube and pulling it into the catheter.

17. The method of claim 16 wherein said capturing and holding means includes a grasping device which begins at handles at one end of said catheter, runs through the lumen of said catheter, and ends in opposing jaws at the other end of said catheter, whereby the jaws of said grasping device may be opened and closed by manipulating the handle end of said grasping means.

18. The method of claim 16 wherein said capturing and holding means is a magnetic means positioned on the end of said catheter.

19. The method of claim 16 wherein said capturing and holding means comprises both a grasping means and a magnetic means for capturing and holding an end of said tube.

20. The method of claim 16 wherein said catheter has light means on the lower end of said catheter to aid in visually locating objects in the patient.

21. A process for controlling the transfer of food chemicals and body fluids with an implanted tube means in a part of a gastrointestinal tract, said implanted tube being contained in its entirety within the gastrointestinal tract while it is implanted, said tube further having physical characteristics by which food chyme within the tube is transported by normal body peristalsis, said process comprising:

a. implanting a thin-walled, open-ended tube totally within at least a part of a gastrointestinal tract for passing digesting food solids through said tube responsive to normal bodily peristaltic contractions, said food solids being the food normally consumed through the mouth of the person with the tube implant, said food further becoming partially digested before coming into contact with and entering into said implanted tube, said implanted tube lining the adjacent intestinal wall to receive the chyme discharged from the tract and into the tube and to control a transfer of said digesting food chemicals and the walls of said gastrointestinal tract; and b. using the implant over an extended period of time while it is totally contained within said gastrointestinal tract for controlling an amount of such chemical transfer.

22. The process of reducing the size of the villi in a gastrointestinal tract by reducing the use of said villi for absorption of food chemicals, said process comprising the steps of:

a. forming a thin-walled, balloon-like tube with a relatively smaller outer diameter when empty of food chemicals b. forming holes in said tube for passing digesting food chemicals to a desired portion of said gastrointestinal villi, whereby said tube reduces the food chemical absorption of said gastrointestinal villi, thereby reducing the size of the villi; and c. implanting said thin-walled, open-ended, balloon-like tube into at least a part of a gastrointestinal tract of a person while said tube is empty and has said small diameter, said balloon-like tube being implanted totally within the gastrointestinal tract with said holes adjacent said desired portion of said villi, whereby no portion of said tube extends away from the body of the person, said balloon-like tube expanding to have a wider effective outer diameter when filled with food chemicals, whereby normal bodily peristaltic motion transports digesting food chemicals through said tube.

23. A method of implanting an instrument for controlling and restricting absorption of food chemicals within a specific intestinal portion of an alimentary canal beginning below the intake to the stomach while enabling other portions of the same intestinal canal to have an unrestricted absorption of food chemicals, said specific portion of said intestine being removed to a point below the exit of the stomach by a predetermined length of said intestine, said method comprising the steps of (a) implanting an open-ended flexible tube which completely collapses at least in part owing to its lack of rigidity, (b) anchoring said tube at a point below the intake to the stomach, said entire instrument including anchoring means completely contained within said stomach and the intestine attached thereto, an end of said tube nearest said stomach being held by said anchor means totally within the intestinal part of the alimentary canal and at a point located said predetermined distance away from the beginning of said intestine, means for joining one end of the tube to said anchor means, said joining means comprising a narrow, elongated device which is impervious to chemicals likely to appear in said intestinal portion of the alimentary canal, whereby said tube restricts absorption in the areas of said alimentary canal which begins at the tube end of said joining means and said tube does not restrict absorption in the area of said alimentary canal between said anchor means and said one end of the tube, said food chemicals being consumed in a solid, non-digested form through the mouth of the person having the implant and becoming partially digested in the stomach before coming into contact with said anchor means and thereafter being squeezed by peristalsis through said tube, and (c) positioning said anchor means to enable said food chemicals to pass from the stomach and into the intestine where they will enter said tube after peristalsis has transported them said predetermined distance beyond said anchor means.

24. The method of claim 23 wherein the anchoring means is a bar-shaped device having a midpoint attached to said elongated device, said bar being generally perpendicular to said device when anchored in place, whereby food chemicals pass over and around said bar before leaving the stomach and entering the intestine.

25. The method of claim 23 wherein the anchoring means is a ring.

26. The method of claim 23 and slow-dissolving means for streamlining an end of said tube which first enters said canal to enable an insertion thereof without snagging, said slow-dissolving means later dissolving in the stomach or intestine.

27. The method of claim 23 wherein said joining means is longitudinally flexible to elongate and contract in response to the gastrointestinal movements, thereby reducing erosion on the portion of said alimentary canal which is used to anchor said implant instrument.

28. The method of claim 27 wherein said means for anchoring said tube includes a float which is supported by the fluid in the stomach.

29. The method of claim 23 wherein said joining means includes as part thereof a spring which elongates and contracts said joining means in response to said gastrointestinal movements.

30. The method of claim 23 wherein said joining means has a spring-tensioned reel means which pays out a cable or reels in a cable to add or reduce length of said joining means in response to the expanding and contracting gastrointestinal tract.

31. The method of claim 23 wherein said tube is a thin, balloon-like tube which begins a predetermined distance from said anchor means which distance is fixed by said joining means, and semi-flexible ring means attached around its circumference to said one end of said tube for holding open said tube to receive digesting food chemicals which enter said tube through said ring.

32. The method of claim 31 wherein said ring is covered with a sponge material passing around the outer circumference of said semi-flexible ring, said sponge material being supple enough to mold itself to the surrounding area of said alimentary canal.

33. The method of claim 23 wherein said tube is a balloon-like tube including a hollow tubular means for receiving an elongated semi-rigid rod or wire which may be inserted through said tubular means to give a more rigid support to said balloon-like tube.

34. The method of claim 23 wherein at least some of the open-ended tube is formed into a porous mesh-type material, with interrupted sections of said mesh-type material impregnated with a material for restricting said absorption.

35. The method of claim 23 wherein large portions of the walls of said tube are open.

36. An implant instrument for controlling and restricting absorption of food chemicals within a specific intestinal portion of an alimentary canal while enabling other portions of the same intestinal canal to have an unrestricted absorption of food chemicals, said specific portion of said intestine beginning at a point which is a predetermined distance below the stomach, said implant instrument comprising an open-ended tube, means for anchoring said tube totally within the intestinal part of the alimentary canal and at a point located said predetermined distance away from the stomach, means for joining one end of the tube to said anchor means, said joining means comprising a narrow, elongated device which is impervious to chemicals likely to appear in said intestinal portion of the alimentary canal, whereby said tube restricts absorption in the areas of said alimentary canal which begins at the tube end of said joining means and said tube does not restrict absorption in the area of said alimentary canal between said anchor means and said one end of the tube, said food chemicals being consumed in a solid, non-digested form through the mouth of the person having the implant and becoming partially digested in the stomach before coming into contact with said anchor means and thereafter being squeezed by peristalsis through said tube, said anchor means having a design which enables said food chemicals to pass from the stomach and into the intestine where they will enter said tube after peristalsis has transported them said predetermined distance, means for inserting and removing said implant instrument in said body, said insert means comprising a catheter having means for capturing and holding an end of said implant instrument while it is being inserted into or removed from said canal and for releasing said implant instrument means after it is implanted, whereby said catheter may be removed while the implant instrument is in place, said catheter having means for curling its end in order to approach the end of said tube, and the ends of said tube and of said catheters having complementary coupling means for seizing the tube and pulling it into the catheter.

37. The instrument of claim 36 wherein said means for curling the end of said catheter includes a series of V-slots and a cord for closing said slots.

38. The instrument of claim 36 wherein said means for curling the end of said catheter is a spring guide.

39. An implant instrument for controlling and restricting absorption of food chemicals within a specific intestinal portion of an alimentary canal while enabling other portions of the same intestinal canal to have an unrestricted absorption of food chemicals, said specific portion of said intestine beginning at a point which is a predetermined distance below the stomach, said implant instrument comprising an open-ended tube, semi-flexible ring means attached around its circumference to said one end of said tube for holding open said tube to receive digesting food chemicals which enter said tube through said ring, said ring being mounted in a track for expanding and contracting relative to the expanding and contracting dimensions of the surrounding area, means for anchoring said tube totally within the intestinal part of the alimentary canal and at a point located said predetermined distance away from the beginning of said intestine, means for joining one end of the tube to said anchor means, said joining means comprising a narrow, elongated device which is impervious to chemicals likely to appear in said intestinal portion of the alimentary canal, said tube being a thin, balloon-like tube which begins said predetermined distance from said stomach, which distance is fixed by said joining means, whereby said tube restricts absorption in the areas of said alimentary canal which begins at the tube end of said joining means and said tube does not restrict absorption in the area of said alimentary canal between said anchor means and said one end of the tube, said food chemicals being consumed in a solid, non-digested form through the mouth of the person having the implant and becoming partially digested in the stomach before coming into contact with said anchor means and thereafter being squeezed by peristalsis through said tube, said anchor means having a design which enables said food chemicals to pass from the stomach and into the intestine where they will enter said tube after peristalsis has transported them said predetermined distance beyond said anchor means.

40. An artificial peristalsis-producing implant instrument for passing digesting food chemicals through the intestine, said digesting food chemicals being consumed in a non-digested form through the mouth of a person having the implanted instrument, the food solids becoming partially digested in the stomach before entering said implant instrument, said implant instrument including an elongated open-ended tube for implantion in the intestine, said tube having passageway for transporting digesting food solids within a smooth and unobstructed surface to enable said digesting food solids to be artificially squeezed through said tube, a plurality of controllable magnetic means integral with and incorporated into a side of the walls of said tube, said opposite wall integrally containing magnetic material which is attracted to said magnetic means when said magnetic means is energized, said plurality of magnetic means being distributed along the entire length of said tube for alternately and periodically attracting the opposite wall of said tube, whereby said walls of the tube are periodically drawn together to reduce the effective cross section of the lumen within said tube, means for selectively energizing said controllable magnetic means for periodically reducing the lumen of said tube, and means for periodically interrupting said energization to eliminate the attraction of said controllable magnetic means to enable the walls of said tube to relax and open the effective cross section of said lumen, and means for causing said attraction and relaxing to occur in a sequence simulating natural peristalsis, whereby said implant instrument artificially squeezes the digesting food solids through said tube in a gradual manner, similar to normal peristalsis, so as not to cause an unnecessary buildup of pressure in the alimentary canal of the person having the implant.

41. An artificial peristalsis-producing implant instrument for passing digesting food chemicals, said digesting food chemicals being consumed in a non-digested form through the mouth of a person having the implanted instrument, the food solids becoming partially digested before entering said implant instrument, said implant instrument including an elongated open-ended tube, said tube having a passageway for transporting digesting food solids within a smooth and unobstructed surface to enable said digesting food solids to be artificially squeezed through said tube, a plurality of controllable magnetic means integral with and incorporated into a side of the walls of said tube, said opposite wall integrally containing magnetic material which is attracted to said magnetic means when said magnetic means is energized, said plurality of magnetic means being distributed along the entire length of said tube for alternately and periodically attracting the opposite wall of said tube, whereby said walls of the tube are periodically drawn together to reduce the effective cross section of the lumen within said tube, means for selectively energizing said controllable magnetic means for periodically reducing the lumen of said tube, means for periodically interrupting said energization to eliminate the attraction of said controllable magnetic means to enable the walls of said tube to relax and open the effective cross section of said lumen, and means for causing said attraction and relaxing to occur in a sequence simulating natural peristalsis, whereby said implant instrument artificially squeezes the digesting food solids through said tube in a gradual manner, similar to normal peristalsis, so as not to cause an unnecessary buildup of pressure in the alimentary canal of the person having the implant.

* * * * *